US007191644B2

(12) United States Patent
Haselhurst et al.

(10) Patent No.: US 7,191,644 B2
(45) Date of Patent: Mar. 20, 2007

(54) SYSTEM INCORPORATING AN INSOLE PRESSURE SENSOR AND PERSONAL ANNUNCIATOR FOR USE IN GAIT ASSISTIVE THERAPY

(76) Inventors: Richard S. Haselhurst, 1126, NE. 16th Ct., Fort Lauderdale, FL (US) 33305; Jon R. Christiansen, 4131 Stirling Rd. #104, Fort Lauderdale, FL (US) 33314

( * ) Notice: Subject to any disclaimer, the term of this patent is extended or adjusted under 35 U.S.C. 154(b) by 0 days.

(21) Appl. No.: 10/897,694

(22) Filed: Jul. 24, 2004

(65) Prior Publication Data

US 2006/0016255 A1 Jan. 26, 2006

(51) Int. Cl.
*A61B 5/00* (2006.01)
*A65B 5/00* (2006.01)

(52) U.S. Cl. .................................................. 73/172

(58) Field of Classification Search .................. 73/172
See application file for complete search history.

(56) References Cited

U.S. PATENT DOCUMENTS 6,031,463 A * 2/2000 Bechmann .................. 73/172
6,195,921 B1 * 3/2001 Truong ........................ 36/136
6,326,539 B1 * 12/2001 Mishima ...................... 84/723
6,377,178 B1 * 4/2002 DeToro et al. ........... 340/573.1
6,752,028 B2 * 6/2004 Bechmann ............. 73/862.391
6,807,698 B2 * 10/2004 Torbet et al. .................. 5/727
6,865,825 B2 * 3/2005 Bailey et al. .................. 36/88

* cited by examiner

*Primary Examiner*—Max Noori
(74) *Attorney, Agent, or Firm*—Needle & Rosenberg P.C

(57) ABSTRACT

A gait assistive system designed to assist with the therapeutic treatment of subjects who have difficulty in walking, specifically those with a lack of sensation due to nerve damage or amputation, who are unable to tell when the foot makes contact with the floor. The system includes a removable insole placed inside the shoe which proportionally senses touchdown of the limb. The sensed touchdown is communicated to a transmitter and subsequently to a remotely positioned receiver to provide a desired bio-feedback of the sensed touchdown. The system can also include a second remotely located receiver that can be used to facilitate set up and/or adjustments of the system.

11 Claims, 3 Drawing Sheets

SYSTEM INCORPORATING AN INSOLE PRESSURE SENSOR AND PERSONAL ANNUNCIATOR FOR USE IN GAIT ASSISTIVE THERAPY

BACKGROUND OF THE INVENTION

One of the problems associated with hip, knee and foot surgery is a loss of sensation in the affected limb. Although the limb may be physically whole and the associated muscles are controllable, visual confirmation of contact between the foot and the ground is necessary. Visual confirmation is also essential in the case of amputation of the limb and certain degenerative conditions due to medical circumstances, eg: diabetes, frostbite, obesity.

Those without sensation in the lower limbs also experience difficulty in operating machinery where vision has to be concentrated on the machine in use, eg: motor vehicle, yard equipment. Activities such as negotiating steps and ladders, stepping backwards, responding to moving objects (e.g.; crossing a road in traffic), walking in darkness or on uneven surfaces and carrying large objects are made much more difficult without sensory feedback from the feet. Quite often, the post-surgical medication given to the patient reduces the patient's ability to concentrate visually on the movement of the feet.

There are also certain medical conditions which preclude a patient from looking downwards to check each step taken, e.g., progressive supranuclear palsy (PSP) and certain balance disorders.

Although there are devices available which will indicate pressure on the foot, they are designed for gait corrective therapy in a clinical environment and are not intended for everyday use. In reality, the only existent remedy for those affected, is to use a cane, or, in the worst cases a wheelchair.

BRIEF SUMMARY OF THE INVENTION

A system for providing biofeedback information to a subject for gait assistive therapy. In one aspect, the system comprising an insole pressure sensor that comprises a lower layer of foam having at least one bottom conductive element mounted to an upper side of the lower layer of foam; a middle layer of foam that defines at least one plurality of holes; a plurality of conductive foam cores that are positioned into the respective holes formed in the middle layer; and an upper layer of foam having at least one upper conductive element mounted to a lower side of the upper layer of foam. In one embodiment, the lower layer of foam is mounted to a bottom surface of the middle layer of foam and the upper layer of foam is mounted to top surface of the middle layer of foam to form a flexible shoe insert.

In a further aspect, each conductive element is in communication with an earpiece worn by a subject such that the subject is informed of their relative gait by the tone changes that are received via the earpiece. In one aspect, the tone provided to the user that indicates that pressure on the ball area of the formed insert exceeds a pre-set level differs from the tone that is received therein the earpiece that indicates that pressure on the heel area of the formed insert exceeds a pre-set level.

In operation, the subject receives an audible or sensory signal indicating that the foot is in contact with the ground. This signal is immediately assimilated by the brain and replaces the missing sensory feedback from the damaged nerves in the foot. This removes the need for visual confirmation, thereby assisting the user to walk normally.

Other apparatus, methods, and aspects and advantages of the invention will be discussed with reference to the Figures and to the detailed description of the preferred embodiments.

BRIEF DESCRIPTION OF THE DRAWINGS

The accompanying drawings, which are incorporated in and constitute a part of this specification, illustrate several aspects described below and together with the description, serve to explain the principles of the invention. Like numbers represent the same elements throughout the figures.

DETAILED DESCRIPTION OF THE INVENTION

Figure 1:
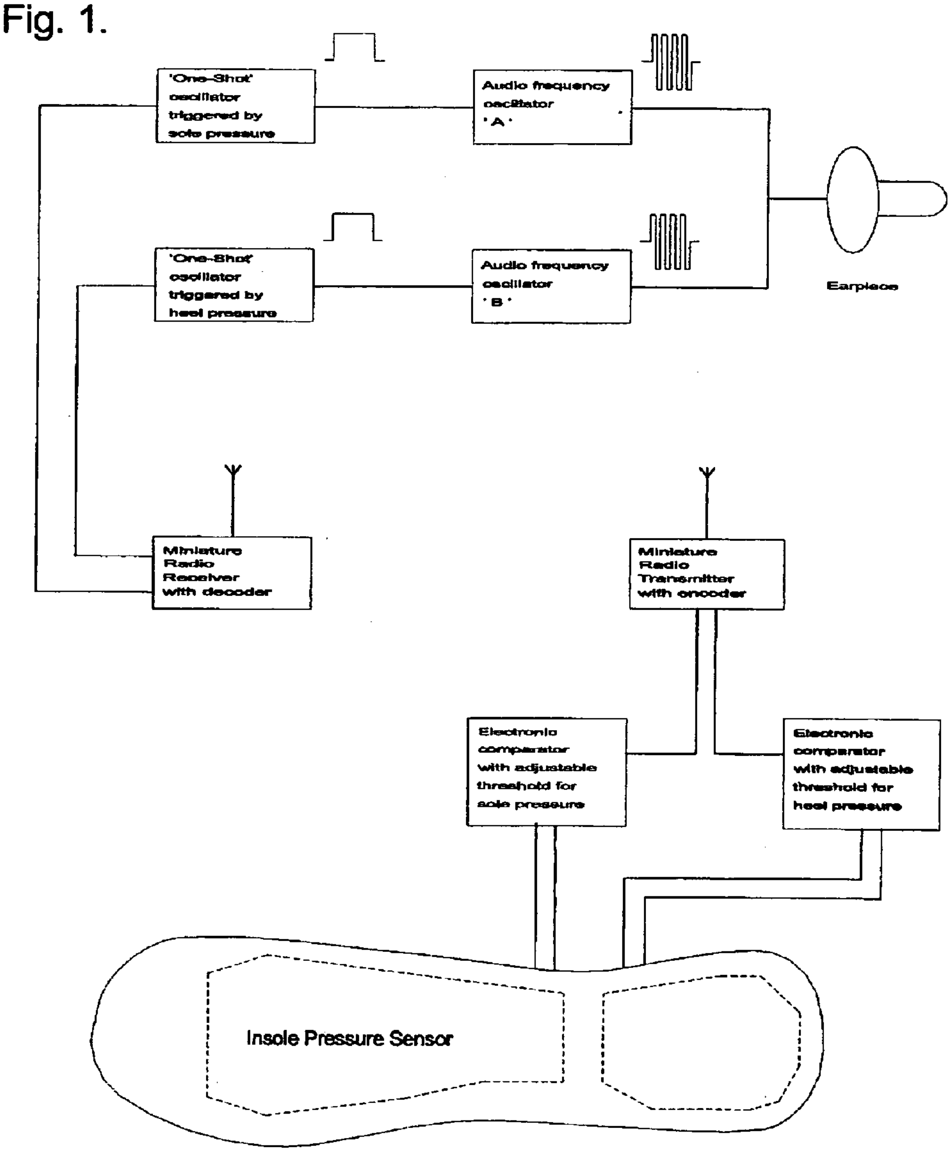
FIG. 1 is a schematic block diagram of the system of the present invention with audible signal output.
Figure 2:
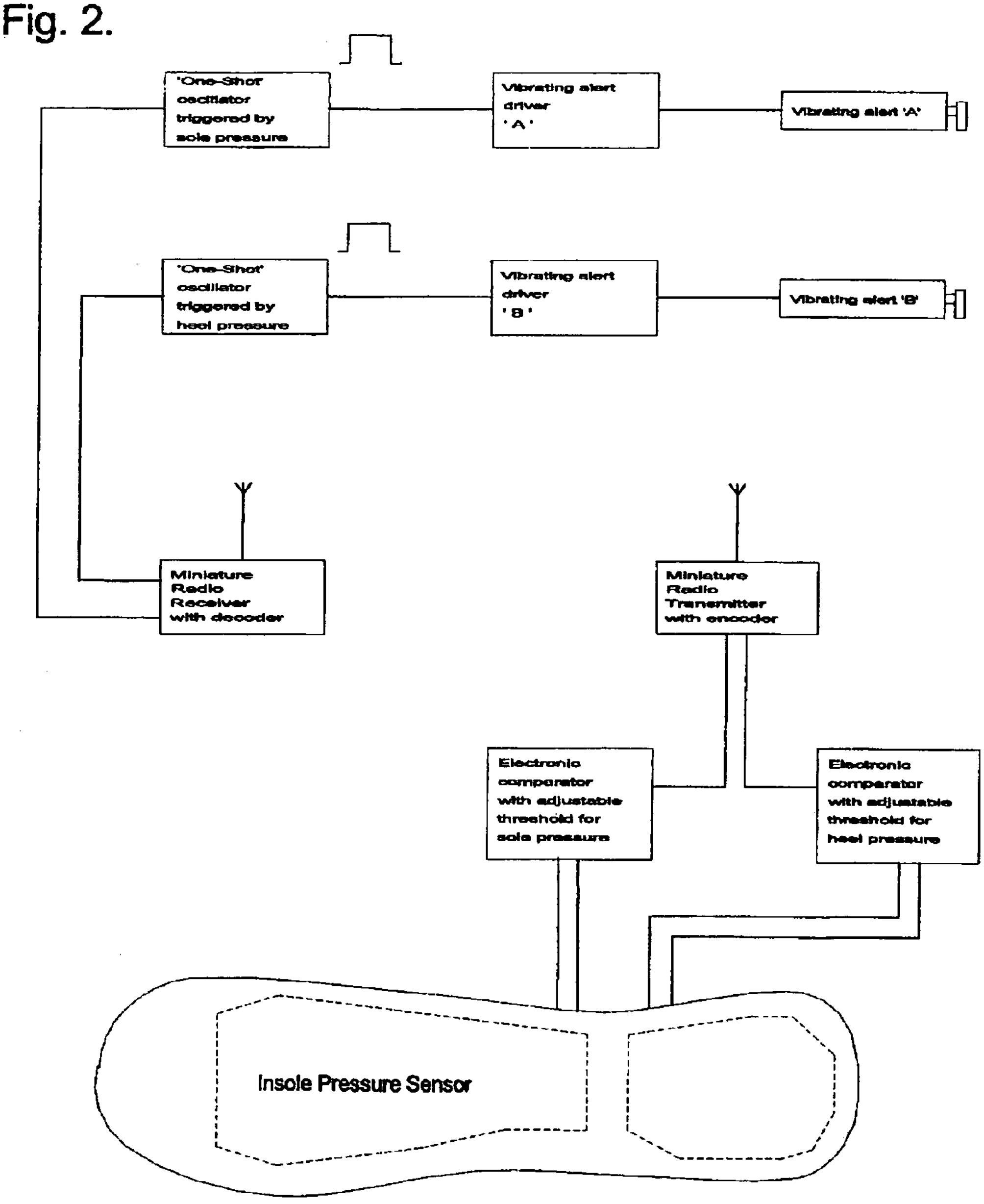
FIG. 2 is a schematic block diagram of the system of the present invention with vibrating signal output.
Figure 3:
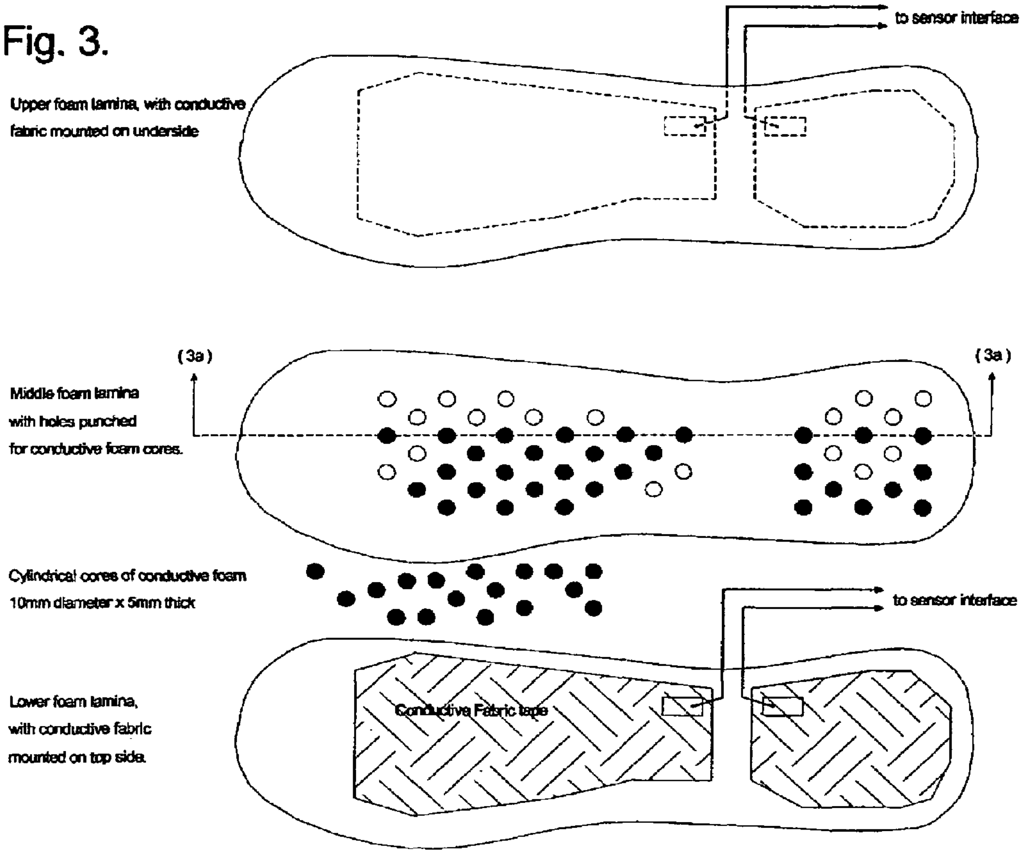
FIG. 3 is a schematic of the construction of an insole pressure sensor.
Figure 3A:
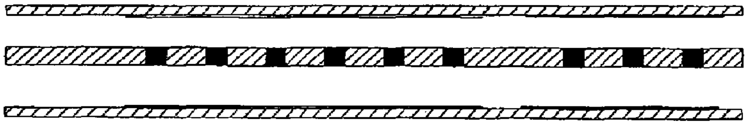

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "an oscillator" can include two or more such osillators unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The present invention may be understood more readily by reference to the following detailed description of preferred embodiments of the invention and the examples included therein and to the Figures and their previous and following description.

In one embodiment, the system of the present invention comprises: a foot pressure sensor; an adjustable threshold sensor interface; an addressable wireless data transmitter; an addressable wireless data receiver; a user interface, and a therapy clinic set-up receiver.

In one aspect, the insole pressure sensor is a composite foam sandwich, comprising three layers:

a.) A lower layer of foam has areas of conductive fabric tape attached to the upper side that corresponds to the separate areas of the sole of the foot to be monitored;

b.) A middle layer of foam has punched holes in a grid pattern in each of the areas of the foot to be monitored, into which cores of conductive foam have been inserted; and c.) An upper layer of foam is a mirror image of the lower layer, with the areas of conductive fabric attached to the lower side of the foam.

Electrical connecting cables are attached to each area of conducting fabric, using conductive silicone glue, and are led out from the area on the inside of the arch of the foot. The sandwich is then glued together to create a one-piece flexible shoe insert, which can be trimmed to fit the patients shoe size. The insole can simply be inverted for use in either left or right shoe.

Each pair of connecting wires from the insole is led to an electronic circuit comprised of an adjustable voltage divider network and a comparator. It is contemplated that the voltage divider network can be adjusted to prevent false signals which may arise from the normal pressure exerted by the foot on the insole when not in contact with the ground.

The pressure required to trigger the comparator can be set to accommodate the loading requirements of individual therapy. In operation, when the pressure on each area of the insole reaches the pre-set level, the comparator changes state and provides a digital output. The digital output from each comparator is encoded and fed to a commercially available addressable miniature wireless transmitter, which can be located in the same enclosure as the comparator circuitry.

The addressable feature of the transmitter is to ensure exclusivity individual systems. In one aspect, the transmitter enclosure is small enough to be worn unobtrusively on the side of the shoe or on the user ankle.

The data from the transmitter is received by a commercially available addressable miniature wireless receiver and is decoded. Each output from the decoder, corresponding to the separate areas of the insole, is fed to a 'one-shot' oscillator which provides a pulse, the length of which can be adjusted to suit the user.

Each 'one-shot' pulse triggers an audio oscillator, the frequency and amplitude of which can be adjusted to suit the user.

In one aspect of the invention, the outputs from each audio oscillator are combined and fed to an earpiece worn by the user. Alternatively, the outputs from the 'one-shot' oscillators can each be fed to a driver circuit which activates a vibrating alert such as used in a mobile pager, to provide a sensory indication of foot 'touchdown'. The vibrating alerts can be worn on any part of the body to suit the user.

In a further aspect of the invention, to assist with initial set-up and adjustment of each users system, the therapist is equipped with a similar addressable receiver, the outputs from which will provide audible signals from a loudspeaker and visual signals from indicator lights which correspond to each of the areas of the insole pressure sensor.

The preceding description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. The corresponding structures, materials, acts, and equivalents of all means or step plus function elements in the claims below are intended to include any structure, material, or acts for performing the functions in combination with other claimed elements as specifically claimed.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification. The blocks in the flow charts described above can be executed in the order shown, out of the order shown, or substantially in parallel.

Accordingly, those who work in the art will recognize that many modifications and adaptations to the present invention are possible and can even be desirable in certain circumstances and are a part of the present invention. Other embodiments of the invention will be apparent to those skilled in the art from consideration of the specification and practice of the invention disclosed herein. Thus, the preceding description is provided as illustrative of the principles of the present invention and not in limitation thereof. It is intended that the specification and examples be considered as exemplary only, with a true scope and spirit of the invention being indicated by the following claims.

What is claimed is:

1. A system for providing biofeedback information to a subject for gait assistive therapy, comprising:

an insole pressure sensor, comprising:

a lower layer of foam having an upper side;

at least one bottom conductive element mounted to the upper side of the lower layer of foam;

a middle layer of foam defining at least one plurality of holes, the at least one plurality of holes comprising a first plurality of holes that are positioned proximate a heel portion of the of the middle layer of foam and a second plurality of holes that are positioned proximate a ball portion of the middle layer of foam;

a plurality of conductive foam cores, wherein one foam core is positioned into each hole of the at least one plurality of holes;

an upper layer of foam having a lower side; and at least one upper conductive element mounted to the lower side of the upper layer of foam, wherein the lower layer of foam is mounted to a bottom surface of the middle layer of foam and the upper layer of foam is mounted to top surface of the middle layer of foam to form a flexible shoe insert.

2. The system of claim 1, further comprising a plurality of electrical traces, wherein one electrical trace of the plurality of electrical traces is in registered communication with one conductive element.

3. The system of claim 1, wherein the conductive element is a conductive fabric.

4. The system of claim 1, wherein the upper and lower layers of foam have substantially the same shape.

5. The system of claim 2, wherein the electrical traces are in communication with a pair of comparators, one comparator of the pair of comparators being in communication with the electrical traces that are mounted therein a ball area of the formed insert and the other comparator of the pair of comparators being in communication with the electrical traces that are mounted therein a heel area of the formed insert, and wherein each of the comparators of the pair of comparators are configured to provide an output signal when the pressure exerted by the subject on the respective ball or heel area of the formed insert exceeds a pre-set level.

6. The system of claim 5, further comprising a transmitter and a receiver that is positioned remotely from the transmitter, and wherein the pair of comparators is in communication with the transmitter such that generated output signal is communicated to the receiver.

7. The system of claim 6, further comprising a pair of first oscillators in communication with the receiver, wherein one first oscillator generates a pulse signal in response to the received output signal when the comparator senses pressure in the ball area of the insert and wherein the other first oscillator generates a pulse signal in response to the received output signal when the comparator senses pressure in the hell area of the insert.

8. The system of claim 7, further comprising a pair of audio oscillators, one audio oscillator being in communication with one first oscillator, wherein each audio oscillator is configured to generate a tone of a pre-set frequency and amplitude in response to the generated pulse signal from the respective first oscillator.

9. The system of claim 8, wherein the pre-set frequency and amplitude of the tone generated by one of the audio oscillators indicates that pressure on the ball area of the formed insert exceeds the pre-set level and the pre-set frequency and amplitude of the tone generated by the other audio oscillator of the pair of audio oscillators indicates that pressure on the heel area of the formed insert exceeds the pre-set level.

10. The system of claim 9, wherein the generated tones of the pair of audio oscillators are different.

11. The system of claim 10, further comprising an earpiece configured to transmit the generated tone to the subject.

* * * * *